US008512226B2

(12) United States Patent
Mark

(10) Patent No.: US 8,512,226 B2
(45) Date of Patent: Aug. 20, 2013

(54) SEXUAL AID DEVICE AND METHOD

(75) Inventor: Lawrence Mark, Port-Of-Spain (TT)

(73) Assignee: Blue Dreams Co. Ltd., Port-of Spain (TT)

( * ) Notice: Subject to any disclaimer, the term of this patent is extended or adjusted under 35 U.S.C. 154(b) by 1064 days.

(21) Appl. No.: 12/520,466

(22) PCT Filed: Dec. 20, 2007

(86) PCT No.: PCT/US2007/088405
§ 371 (c)(1), (2), (4) Date: Jun. 19, 2009

(87) PCT Pub. No.: WO2008/077144
PCT Pub. Date: Jun. 26, 2008

(65) Prior Publication Data

US 2009/0281373 A1 Nov. 12, 2009

Related U.S. Application Data

(60) Provisional application No. 60/871,000, filed on Dec. 20, 2006.

(51) Int. Cl.
*A61F 5/00* (2006.01)

(52) U.S. Cl.
USPC .......................................................... 600/38

(58) Field of Classification Search
USPC ............................. 600/38–41; 128/830–841
See application file for complete search history.

(56) References Cited

U.S. PATENT DOCUMENTS

| | | | |
|---|---|---|---|
| 4,198,976 | A | 4/1980 | Drobish et al. |
| 4,553,965 | A | 11/1985 | Conn et al. |
| 4,920,986 | A | 5/1990 | Biswas |
| 5,819,742 | A | 10/1998 | Sokal et al. |
| 6,328,991 | B1 | 12/2001 | Myhling |

FOREIGN PATENT DOCUMENTS

| | | |
|---|---|---|
| CA | 2491249 | 6/2006 |
| CN | 2218556 | 1/1996 |
| CN | 2430153 | 5/2001 |
| CN | 2699871 | 5/2005 |
| WO | 2006063461 | 6/2006 |

*Primary Examiner* — John Lacyk
(74) *Attorney, Agent, or Firm* — Johnson & Martin, P.A.; James David Johnson

(57) ABSTRACT

A sexual aid device and method for inserting and occupying space within a human female's vagina to provide a sensation of increased fullness to the female and a sensation of increased tightness and friction to a penis of a human male during sexual intercourse, thereby enhancing sexual arousal of both the female and the male. The sexual aid can be a member having a bulbous end for insertion and a tapered end for externally grasping and manipulating the member. The tapered end may include a hooked protrusion for providing anal stimulation to the female. The member may contain one or more vibrating devices. The member may further include a generally planar surface featuring a trough and can include two arced terminuses oriented in opposing directions. An internal pellet-rotating device may be installed within the tapered end of the member to produce mechanical friction in and around the vagina.

19 Claims, 11 Drawing Sheets

SEXUAL AID DEVICE AND METHOD

FIELD OF THE INVENTION

The invention relates to methods and devices for increasing human sexual arousal. More particularly, the invention relates to methods and devices for occupying excess interior space within a human vaginal cavity for enhancing penile and vaginal stimulation during sexual intercourse.

BACKGROUND

For many reasons, including those related to genetics, age, number of pregnancies and childbirths, and personal sexual activity, some human females have been known to experience an enlargement of the vaginal cavity. As the muscles of the vaginal wall lose their tautness and as the vagina enlarges so that vaginal tightness decreases, the female may experience a decrease in sexual satisfaction and sensation. Moreover, the male may also experience a corresponding decrease in sexual satisfaction and sensation due to the lack of tightness and pressure on and around the penis while the penis is inserted into the vagina during sexual intercourse. These problems often center around the loss of friction that follows an increase in the size or volume of the vagina.

Previously, physicians have recommended that females experiencing the loss of vaginal tightness engage in Kegel exercises to increase the tightness of the vagina. However, these muscle exercises have not proven to be effective for many women. Females may also undergo expensive and medically risky vaginoplasty to decrease the diameter of the vagina so as to increase vaginal tightness. However, many women and their sexual partners may be reluctant to select surgery as a solution due to the inherent risks of the procedure involved.

SUMMARY

The invention relates to the development of a sexual aid that features a member that is removably insertable into a vagina of a human female. The insertable member occupies space within the vaginal cavity and thereby reduces the volume of unoccupied space inside the vagina. By leaving the insertable member in the vagina during sexual intercourse, the female can experience a more pleasurable, fuller sensation within the vagina. Likewise, the male can experience a more pleasurable sensation of increased tightness and pressure against the penis while the penis is inserted within the vagina.

The insertable member can be a unitary, generally solid, elongated member that may be removably inserted into the vagina of the female to occupy space so as to reduce the volume of free space within the vagina during sexual intercourse. The insertable member may further include a tapered end and a bulbous end. The bulbous end may be larger in diameter and circumference than the tapered end and can be used for insertion into the vagina. One or both of the bulbous and tapered ends may include diverging tips for providing stimulation to the nerve endings present within the vaginal wall as well as to the female's perineum.

The insertable member can be inserted into the vagina either before or during sexual intercourse to fill a portion of the unoccupied space within the vaginal cavity. During intercourse, when the male inserts his penis into the vagina, the decreased volume or free space available between the insertable member and an anterior portion of the vaginal wall provides the male with an increased sensation of tightness within the vagina, and thus, greater stimulation and pleasure. The thickened bulbous shape of the bulbous end of the insertable member as well as the diverging tip of the bulbous end stimulate the nerves contained within the vaginal wall to provide increased stimulation of the female during intercourse. The female also experiences a sensation of greater fullness during intercourse when both the male's penis and the insertable member are inserted within the vagina. By reducing the void space in the vaginal cavity in women, and particularly in women having a vaginal void with a volume greater than the average female, the insertion member can increase the tactile pressure on the male's penis and against the vaginal wall, thereby, enhancing stimulation of the couple in coitus.

An advantage of the insertable member is that the unoccupied volume present within the vagina during sexual intercourse can be safely and comfortably reduced to enhance the sexual stimulation of a female and male engaged in sexual intercourse. Another advantage of the insertable member is that the member may eliminate the medical need or personal desire of some females to undergo expensive and risky surgical procedures to reduce the size and to increase the tautness of the vagina. Still another advantage of the insertable member is to increase tactile pressure on a penis and against a vaginal wall during intercourse for enhanced sexual stimulation of married people. Yet another advantage of the insertable member is to enhance the sexual satisfaction and sensation for a woman so that her male sexual partner may forgo any medical need or personal desire to undergo surgical penile enhancement procedures to increase the circumference of the penis.

Accordingly, the invention features a sexual aid including an insertable member for removably inserting into a vagina of a human female. The insertable member includes a tapered end that is grasped to insert the insertable member into the vagina and a bulbous end that is inserted into the vagina. The bulbous end occupies space thereby reducing the volume of unoccupied space inside the vagina.

In another aspect, the invention features the insertable member being generally elongated, rounded, and flattened in shape, wherein the tapered end is about 1.9 centimeters thick and the bulbous end is about 3.8 centimeters thick.

In another aspect, the invention features the insertable member constructed from silicone.

In another aspect, the invention features the insertable member constructed from a memory foam enveloped by an exterior elastomer coating.

In another aspect, the invention features the memory foam being a latex memory foam and the exterior elastomer coating being a latex rubber.

In another aspect, the invention features the insertable member including a tapered end having a first arced terminus that curves in a first direction and a bulbous end having a second arced terminus that curves in a second direction that is opposite to the first direction.

In another aspect, the invention features the tapered end including a hooked protrusion having a spherical terminus.

In another aspect, the invention features the hooked protrusion being oriented toward the bulbous end.

In another aspect, the invention features the insertable member being sigmoidal in shape.

In another aspect, the invention features the insertable member further including at least one vibrating device.

In another aspect, the invention features the tapered end including an internal vibrating device.

In another aspect, the invention features the bulbous end including an internal vibrating device.

In another aspect, the invention features the spherical terminus including an internal vibrating device.

In another aspect, the invention features the vibrating device further including a receiver for operation by a remote control.

In another aspect, the invention features the insertable member including a generally planar portion.

In another aspect, the invention features the tapered end including an internal pellet-rotating device.

In another aspect, the invention features the insertable member being trough-shaped and including a trough defined in a top side.

In another aspect, the invention features the insertable member being longer than a penis of a male and extending a greater distance into the vagina than the male's penis when used during sexual intercourse between the female and male.

A method of the invention includes the steps of inserting a member into a vagina of a human female to occupy space within the vagina, and maintaining the member inserted within the vagina while the vagina is penetrated by a human penis during sexual intercourse.

Another method of the invention includes the steps of inserting a bulbous end of the member that includes a first arced terminus into the vagina so that the first arced terminus is oriented toward and contacts an anterior portion of a wall of the vagina, and orienting a tapered end of the member that includes a second arced terminus so that the second arced terminus protrudes out of the vagina and curves toward the female's anus.

Another method of the invention includes the step of inserting the penis into the vagina while the member is inserted within the vagina so that the penis contacts both an anterior portion of a wall of the vagina and a generally planar portion of the member.

Another method of the invention includes the step of including a vibrating device in a bulbous end of the member and stimulating a Gräfenberg spot inside the vagina using the vibrating device.

Another method of the invention includes the step of including a vibrating device in a bulbous end of the member and stimulating an anterior portion of a wall inside of the vagina.

Another method of the invention includes the step of including a vibrating device in a bulbous end of the member and stimulating the penis while the penis is inserted into the vagina during sexual intercourse.

Another method of the invention includes the step of including a vibrating device in a tapered end of the member and stimulating a clitoris of the vagina.

Another method of the invention includes the step of including a vibrating device in a hooked protrusion of the member and stimulating an anus of the human female.

Another method of the invention includes the step of including a pellet-rotating device in a tapered end of the member and stimulating a clitoris of the vagina by mechanical friction as a plurality of pellets are mechanically rotated by a motorized blade within the pellet-rotating device thereby causing changes in the texture of an exterior surface of the member.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control.

DETAILED DESCRIPTION

In one aspect, the invention provides a sexual aid device that includes an insertable member for inserting into a human female's vagina. The insertable member can be inserted into the vagina and kept in position within the vagina while a human male inserts a penis into the vagina for the performance of sexual intercourse. The insertable member occupies space within the vagina that might otherwise be unoccupied during sexual intercourse. As a result, the female experiences a sensation of greater fullness within the vagina while the male experiences a sensation of increased tightness within the vagina during sexual intercourse.

Figure 1:
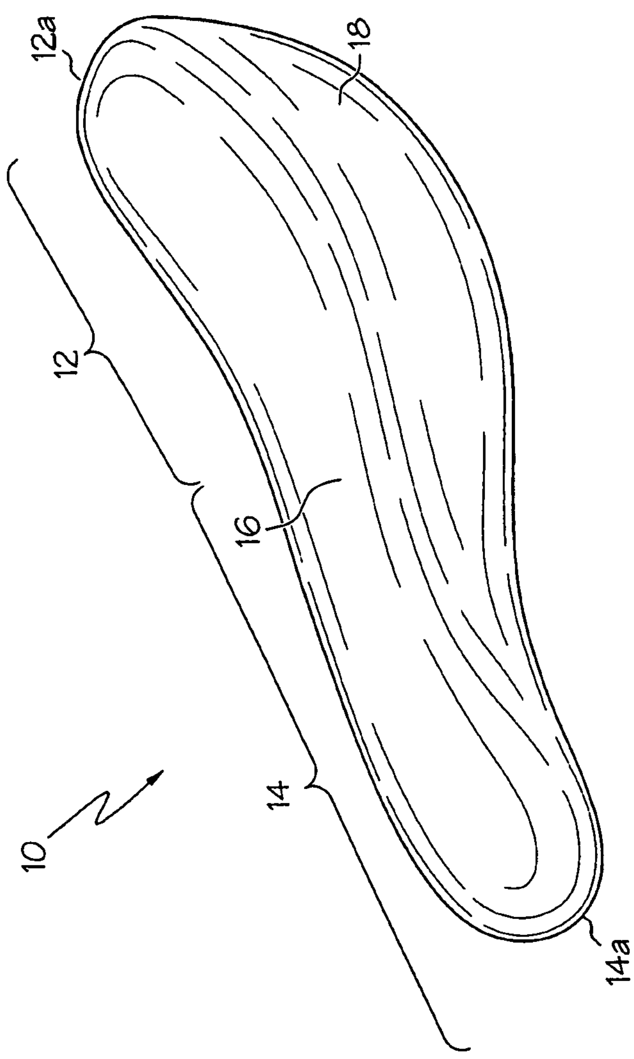
FIG. 1 is a perspective view of an insertable member.
Figure 2:
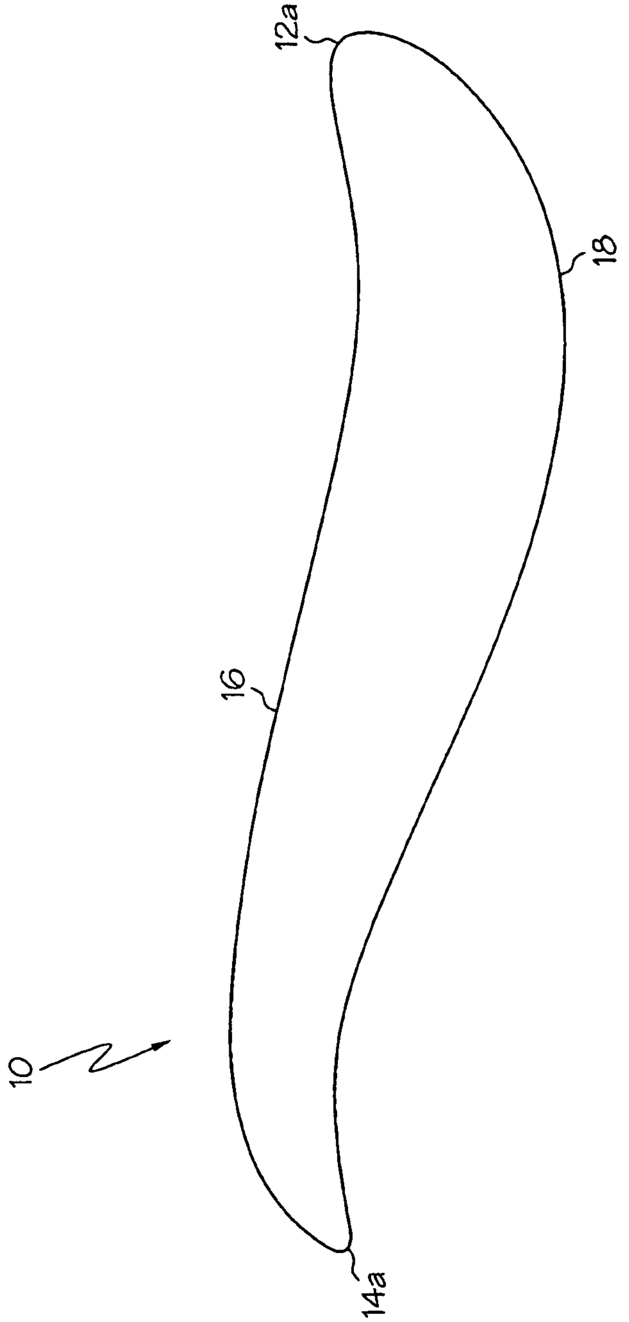
FIG. 2 is a side elevational view of the insertable member of FIG. 1.
Figure 3:
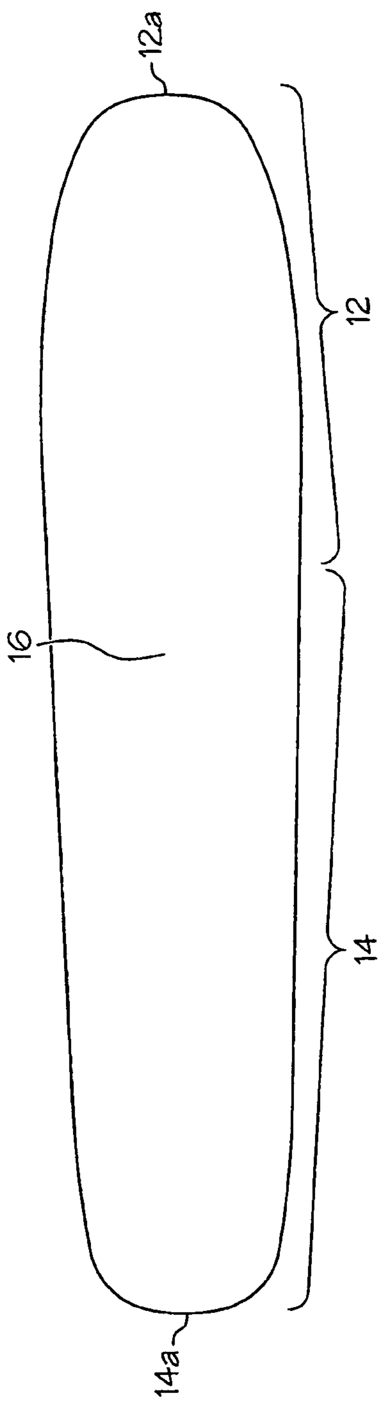
FIG. 3 is a top plan view of the insertable member of FIG. 1.

As illustrated in FIGS. 1-3, the insertable member 10 can be a unitary, single-piece, elongated member having a thickened, bulb-shaped (bulbous) end 12 and a tapered end 14. The tapered end 14 may be manually grasped to insert the insertable member 10 into the vagina. The bulbous end 12 of the insertable member 10 is removably insertable into the vagina and can remain inserted within the vagina during sexual intercourse.

In one embodiment, shown in FIG. 2, the tapered end 14 may include a first arced terminus **14*a* that curves in a first direction. Similarly, the bulbous end 12 may include a second arced terminus 12*a* that curves in a second direction that is opposite to the first direction. The first arced terminus 14*a* and the second arced terminus 12*a* may diverge away in opposite directions from a longitudinal axis of the insertable member 10** so that the insertable member is generally sinusoidal or sigmoidal in shape.

The bulbous end 12 may be larger in overall size and circumference (e.g., about 30, 40, 50, 60, 70, 80, 90, 100, 125, 150, or 200 percent larger) than the tapered end 14 of the insertable member. The circumference of the bulbous end 12 may increase as the distance from the tapered end 14 increases. The bulbous end may taper slightly at the curvature of the second arced terminus 12*a*. The circumference of the insertable member 10 can be greatest at the bulbous end 12 immediately preceding the second arced terminus 12*a*. The bulbous shape of the thickened bulbous end 12 may aid in preventing the insertable member 10 from becoming dislodged and sliding out of the vagina during intercourse.

Figure 4B:
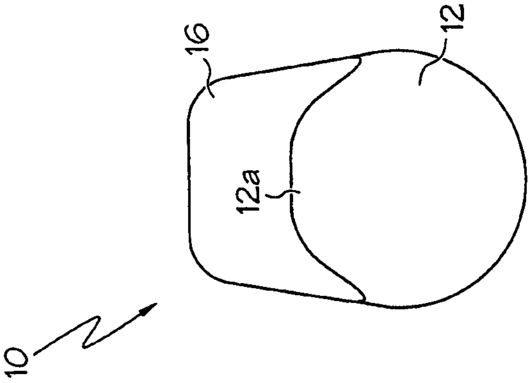
FIG. 4B is a rear elevational view of a bulbous end of the insertable member of FIG. 1.
Figure 4A:
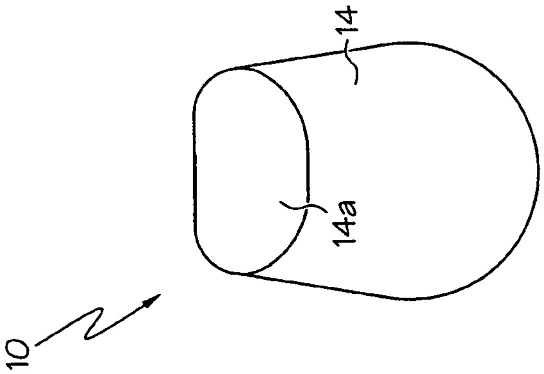
FIG. 4A is a front elevational view of a tapered end of the insertable member of FIG. 1.

As illustrated in FIGS. 1, 2, and 4B, the tapered end 14 of the insertable member 10 can be smaller in overall size and circumference than the bulbous end 12. The first arced terminus 14*a* of the tapered end 14 also curves or diverges away from the longitudinal axis of the insertable member 10 in a direction opposite that of the divergence or curvature of the bulbous end 12. During usage, the first arced terminus 14*a* may protrude from the vagina and can curve toward the female's anus while maintaining contact with the skin of the female's perineum. The importance of the shape and curvature of the tapered end 14 of the insertable member 10 is two-fold. First, the curvature of the first arced terminus 14*a* of the tapered end 14 may prevent the insertable member 10 from blocking access to the vagina. The first arced terminus 14*a* may also prevent any undesirable or uncomfortable contact with or hindrance of movement of the male's genitalia during sexual intercourse.

Second, the curvature of the first arced terminus 14*a* of the tapered end 14 may ensure contact with and stimulation of the female's perineum, which is considered to be an erogenous zone.

As shown in FIGS. 2 and 3, the insertable member 10 can include a top side 16 that forms a generally planar portion for contact with the male's penis during intercourse. Alternatively, the top side 16 may be curved or rounded. The insertable member 10, and particularly the bulbous end 12, can be lubricated prior to usage using any commercially available sexual lubricant.

Figure 9:
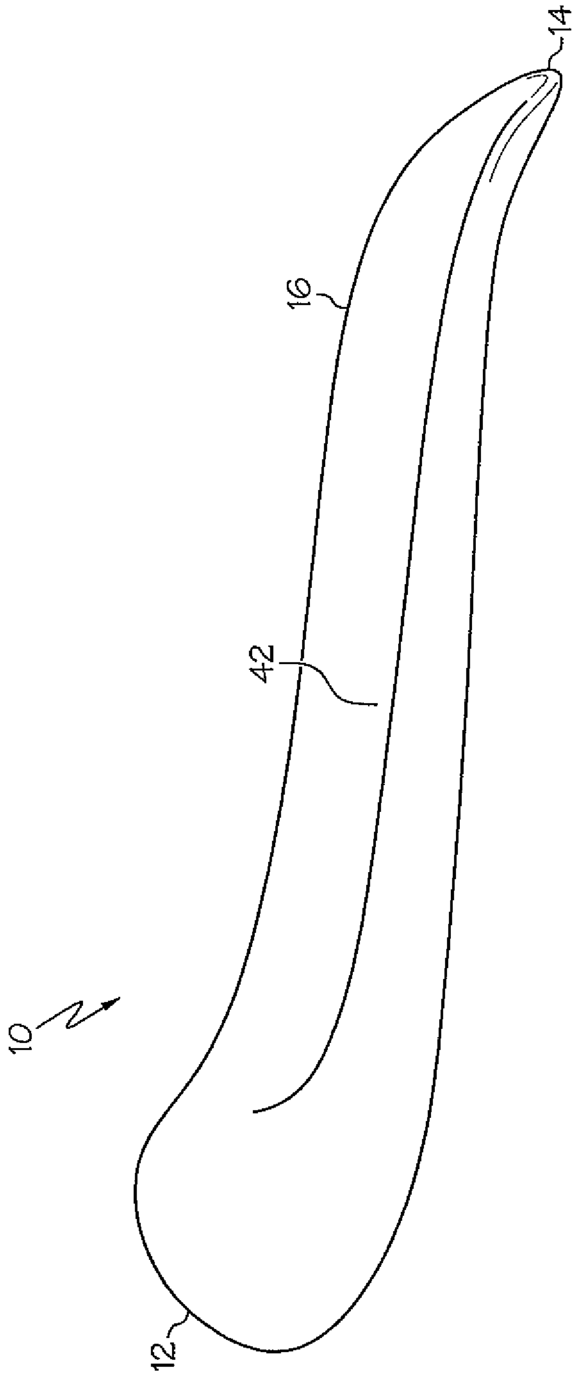
FIG. 9 is a perspective view of an insertable member that is trough-shaped.

In an exemplary embodiment, shown in FIG. 9, the insertable member 10 can be trough-shaped so that the top side 16 features a trough 42 or channel for receiving and contacting the male's penis during sexual intercourse when both the penis and the insertable member are inserted into the female's vagina. The trough 42 may begin at the tapered end 14 and terminate at the bulbous end 12. The bulbous end 12 of the insertable member 10 can extend beyond the length of the trough 42 as shown in FIG. 9 so as to artificially extend the length or depth of the male's penetration of the female's vagina. The insertable member 10 can be longer than the male's penis to allow deeper penetration of the female's vagina by the insertable member. The trough 42 may vary in width at different points along its length or may have generally the same width across its entire length. As the male's penis moves within the trough 42 of the insertable member 10, the insertable member is moved within the female's vagina, thereby creating frictional stimulation for both the male and the female.

Figure 5:
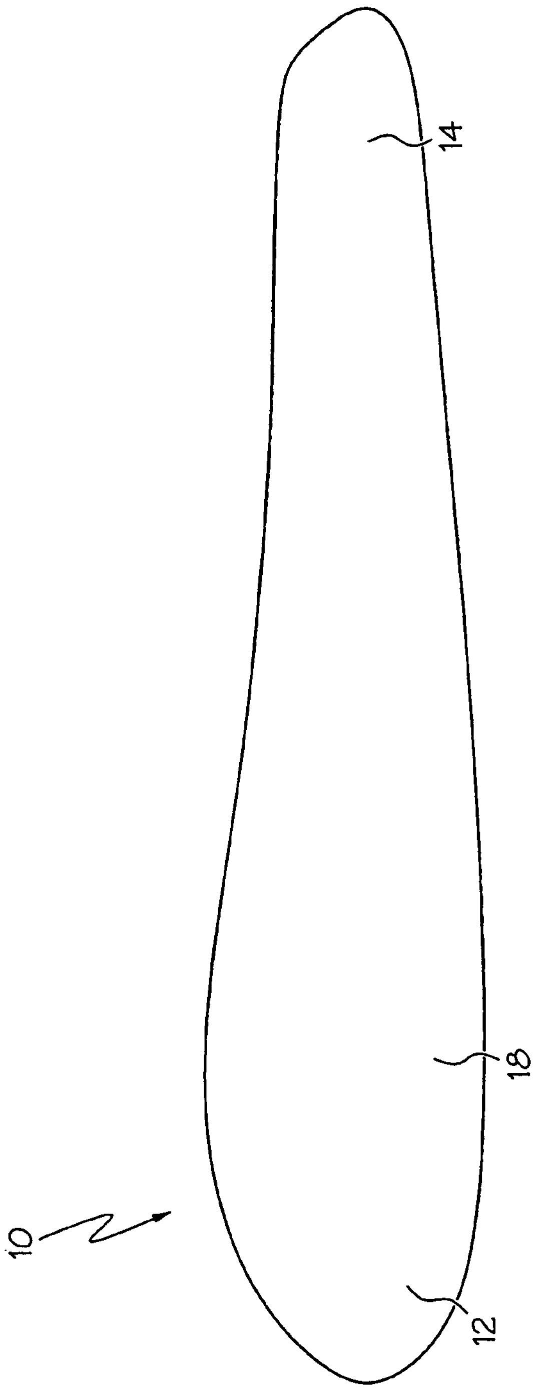
FIG. 5 is a side elevational view of one embodiment of an insertable member.

In an alternate embodiment of the device, shown in FIG. 5, the insertable member 10 can be phallus-shaped. In this embodiment, the bulbous and tapered ends 12 and 14 of the insertable member 10 lack the first arced terminus 14*a* and the second arced terminus 12*a* that may be present in the exemplary embodiment of the insertable member shown in FIGS. 1-4B. The bulbous end 12 may include a thickened portion 18 that converges to seamlessly join the tapered end 14.

In alternate embodiments, the insertable member may be constructed in other elongated, insertable shapes that may be inserted into a human vagina to remain in place within the vagina during sexual intercourse so as to provide a fuller sensation to the female and a tighter sensation to the male within the vagina, thereby enhancing sexual stimulation of the genitalia and other erogenous zones of both the male and female. For example, the insertable member 10 may be cylindrical, trough-shaped, biconcave, biconvex, polygonal, irregular, or star-shaped in cross-section. The insertable member can be generally smooth in texture and any edges present in the aforementioned alternate embodiments may be rounded to provide comfortable use within the vagina and while in contact with the penis.

Figure 6:
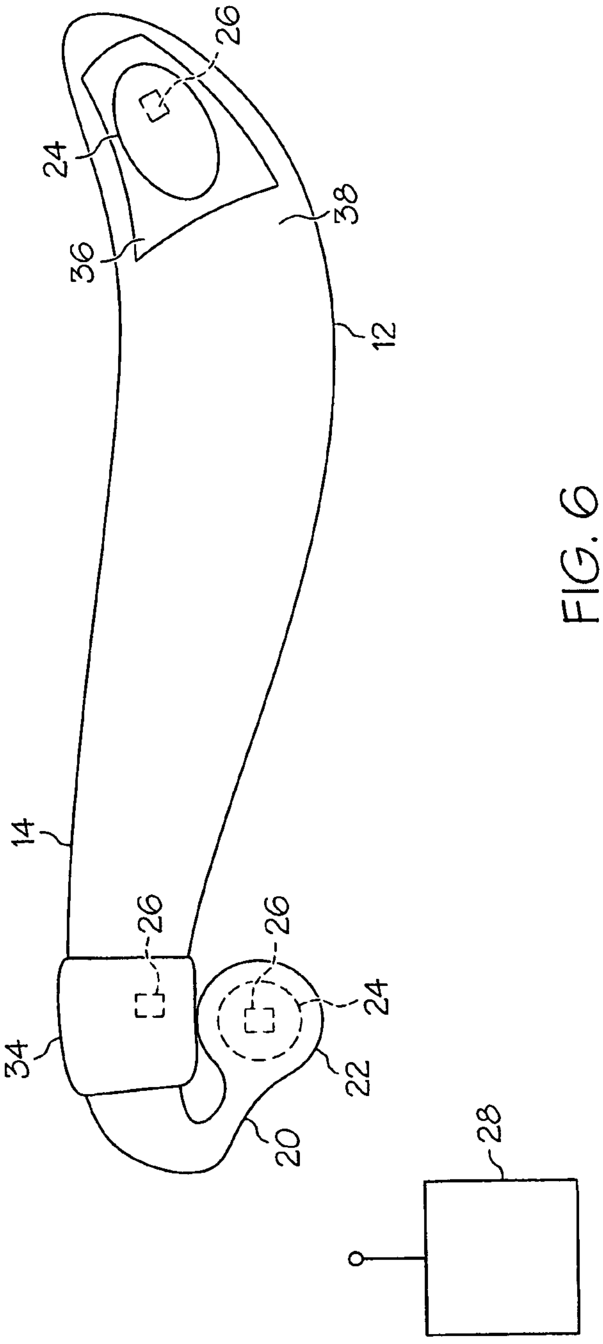
FIG. 6 is a side elevational view of one embodiment of an insertable member including remotely controlled vibrating and massaging devices and a partial cut-away that reveals the core material of the insertable member.

The insertable member 10 can be constructed from a rubber or elastomer material that is medically safe for human usage and from other suitable materials, such as plastic. In an exemplary embodiment, the material used for construction of the insertable member can be hypoallergenic. As shown in FIG. 6, the insertable member may include a core material 36 that can be constructed from medically-safe silicone or from latex memory foam. In embodiments where the core material 36 is composed of silicone or latex memory foam, the core material can be enveloped, in whole or in part, by an exterior elastomer coating 38, for example, latex rubber. When constructed from latex memory foam, the foam changes shape as the insertable member is inserted to accommodate the shape of the vagina. The foam also compresses to accommodate the penis once the penis is inserted into the vagina. When the penis is removed from the vagina, as well as when the insertable member itself is removed from the vagina, the memory foam expands to regain its original shape. The insertable member may also be constructed with a smooth or textured surface. In an exemplary embodiment, the insertable member may be only slightly flexible or bendable. Alternatively, the insertable member may be constructed from materials that are entirely flexible or bendable or from materials that are mostly rigid.

The insertable member 10 may be manufactured in various lengths and thicknesses. The insertable member 10 can be about 23 centimeters (e.g., about 15, 18, 20, 21.5, 23.5, 24, 25, 28, 30, or 33 centimeters) in length. The thickened portion 18 of the bulbous end 12 can be about 3.8 centimeters (e.g., about 2.5, 3.2, 3.5, 4, 4.4, 5, 5.7, or 6.5 centimeters) in thickness as measured beginning at and passing through the top side 16 of the insertable member 10. The tapered end 14 can be about 1.9 centimeters (e.g., about 1.3, 1.5, 1.6, 1.7, 1.8, 2, 2.1, 2.2, or 2.5 centimeters) in thickness as measured from the generally planar portion of the top side 16.

The insertable member 10 may also be constructed with a projection for causing simultaneous anal stimulation of the female anus. In one embodiment, the projection may cause both anal stimulation and anal penetration of the female anus during usage. In an exemplary embodiment shown in FIGS. 8A-B and 8D, the tapered end 14 of the insertable member may include a hooked protrusion 20. The hooked protrusion 20 may include a spherical terminus 22 as featured in FIGS. 8A-8D. The hooked protrusion 20 and spherical terminus 22 can be oriented so that the spherical terminus points in the direction of the bulbous end 12 of the insertable member 10. In this way, the spherical terminus 22 of the hooked protrusion 20 may contact and stimulate the female's anus while the insertable member 10 is inserted inside of the vagina.

In another embodiment, the hooked protrusion 20 may extend off of the first arced terminus 14*a* of the tapered end 14. The hooked protrusion 20 can be oriented toward the bulbous end 12 in a third direction that is generally perpendicular to the first direction and opposite to the second direction.

Figure 7:
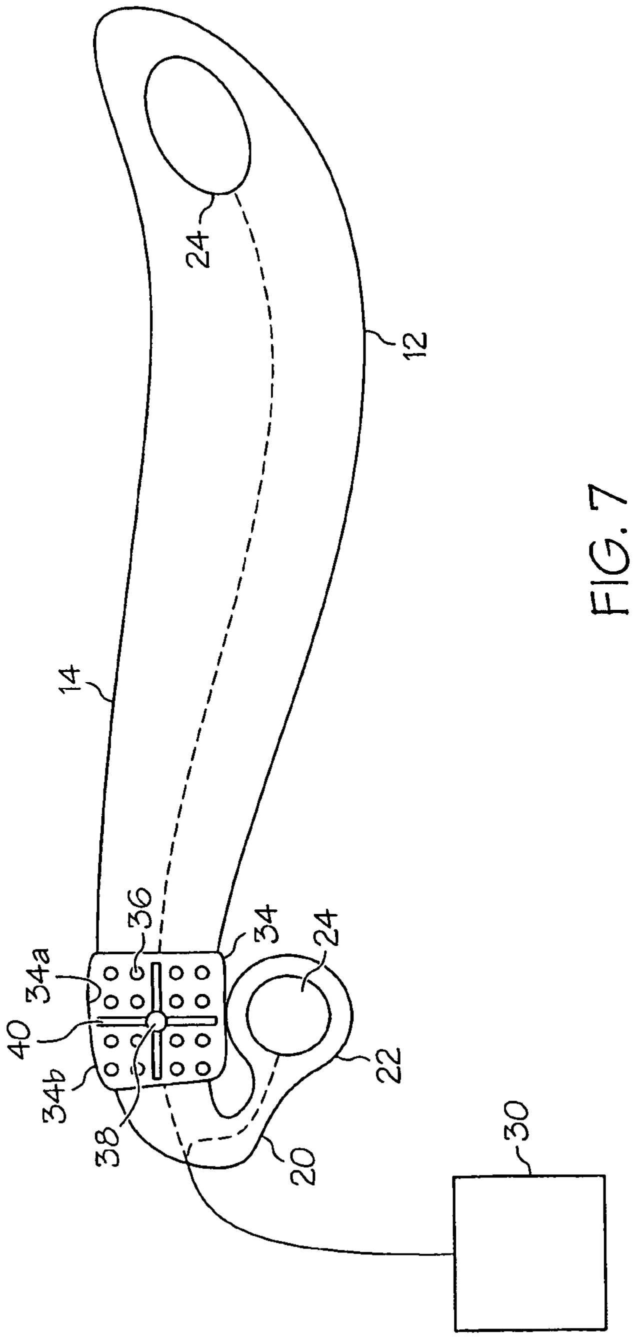
FIG. 7 is a side elevational cut-away view of one embodiment of an insertable member including a hard-wired controller for vibrating and massaging devices.

In other alternate embodiments, the insertable member 10 may also include devices to produce vibration of the insertable member. For example, the insertable member 10 may include one or more vibrating devices 24, as shown in FIGS. 6 and 7, in one or more of the tapered end 14, the bulbous end 12, and in the spherical terminus 22. The vibrating devices 24 can be installed internally within the insertable member 10. Each vibrating device 24 can include a control. In an exemplary embodiment, shown in FIG. 6, the vibrating device 24 includes a receiver 26 that can receive instructions for activating and operating the vibrating device from a remote control 28. In another embodiment, shown in FIG. 7, the vibrating device 24 may be electrically connected (or hardwired) to a controller 30. The vibrating device 24 may include different speed settings for increasing and decreasing the frequency of the vibrations produced. In the remote-controlled and hardwired embodiments, the speed settings may be controlled by the controller 28 or 30.

Figure 8A:
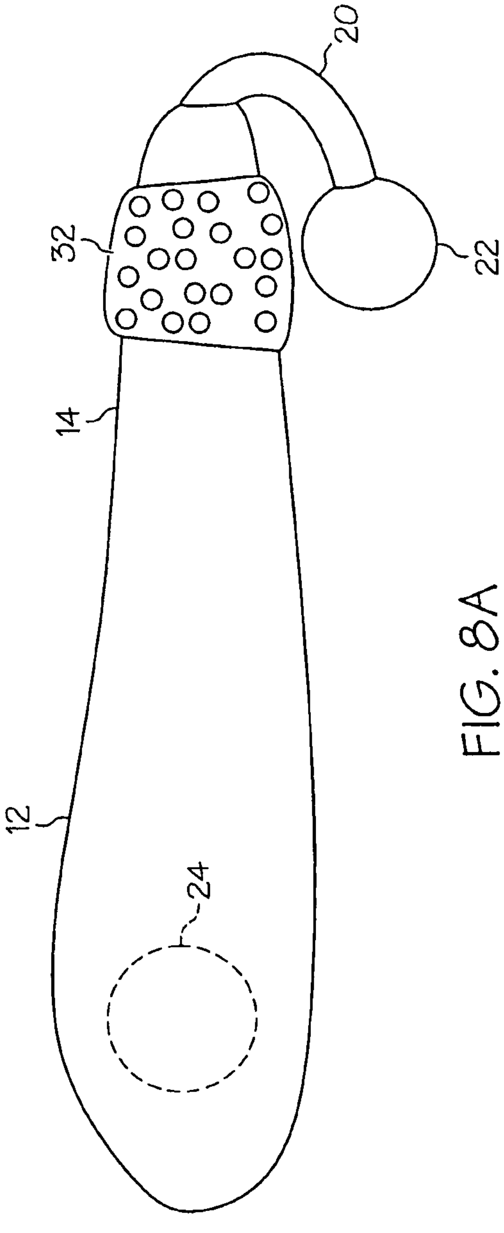
FIG. 8A is a side elevational view of one embodiment of an insertable member having a hooked protrusion.
Figure 8B:
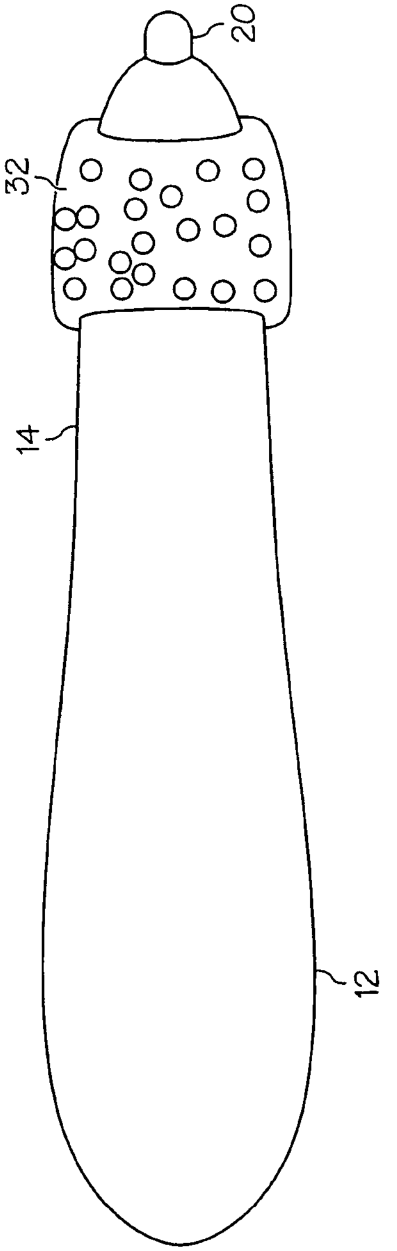
FIG. 8B is a top view of the insertable member of FIG. 8A.
Figure 8D:
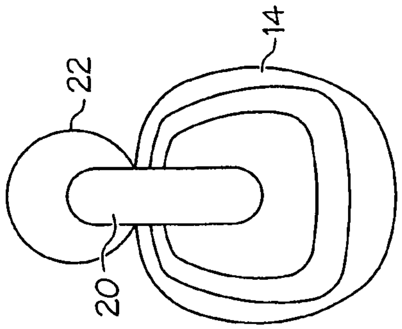
FIG. 8D is a rear view of the insertable member of FIG. 8A showing a tapered end and hooked protrusion of the insertable member.
Figure 8C:
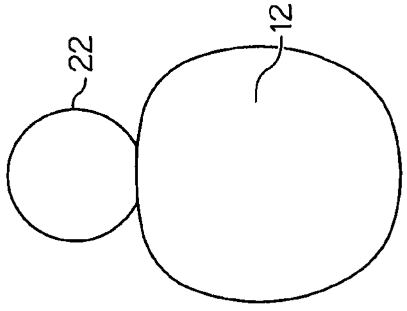
FIG. 8C is a front view of the insertable member of FIG. 8A showing a bulbous end of the insertable member.

In another embodiment, the insertable member 10 may include a massaging device 32, featured in FIGS. 6, 7, and 8A, to produce a massaging motion or friction that can be perceived by the female, and in some embodiments, by the male. The massaging device can be a pellet-rotating device 32. The pellet-rotating device 32 can include a casing 34 for holding a plurality of solid or semi-solid pellets 36 and a motor 38 for rotating a blade 40 disposed within the casing. The casing 34 can be constructed from a flexible material. As the blade 40 rotates, the pellets 36 are moved about inside the casing 34, the pellets move against an interior surface 34*a* of the casing which causes corresponding changes in the texture and shape of an exterior surface 34*b* of the casing. This movement of pellets and changes in the texture and shape of the casing can produce a massaging action or frictional action that may increase the stimulation of vagina. The pellet-rotating device 32 can be controlled via either the hard-wired controller 30 or may include a receiver 26 so as to be controlled by the remote control 28 used to control the vibrating device 24.

In still another embodiment, the insertable member 10 may include a device for rotating the insertable member while it is inserted within the vagina.

In an alternate embodiment, the tapered end 14 of the insertable member 10 may include connected straps that can be fitted around the female's waist or hips to maintain the position of the insertable member inside the vagina. The straps may be permanently or removably connected to the insertable member.

In another alternate embodiment, the insertable member 10 may be removably connected to the base of the male's penis using a ring attached to the tapered end 14 of the insertable member that is fitted over the male's erect penis. The ring may be elastic to flexibly accommodate penises of varying sizes. This embodiment permits movement of the insertable member into the vagina in tandem with the erect penis during sexual intercourse.

In still another alternate embodiment, the insertable member 10 may be inserted along with the male's erect penis into a condom. During intercourse, the insertable member can move in tandem with the erect penis as the penis is inserted into the vagina.

In still another alternate embodiment, the insertable member 10 may include multiple closely-spaced bulbous end portions rather than only a single bulbous end as described in the aforementioned embodiments.

The invention also provides a method for removably inserting an insertable member into a vagina of a human female to fill and occupy part of the free, unoccupied space and volume of a vaginal cavity so that the unoccupied volume of the vaginal cavity can be reduced. By partially filling the vaginal cavity, and thereby, reducing the open space or dimensions of the vaginal cavity, the female experiences a fuller, more pleasurable sensation against a vaginal wall during intercourse while the male experiences a tighter sensation around and against the penis. These effects of usage of the insertable member increase stimulation for both male and female. Because the thickness of the insertable member increases as distance to the tapered end increases, the male experiences increased tightness and increased stimulation as the depth of insertion of the penis into the vagina increases.

The insertable member can be kept inserted within the vagina during sexual intercourse so that the penis is caused to contact and is somewhat compressed against a thicker portion of a bulbous end that precedes a second arced terminus of the bulbous end. During sexual intercourse, the second arced terminus can also direct movement of the penis upward toward a top, or anterior portion, of the vaginal wall for contact with the female's Gräfenberg spot to increase stimulation and arousal of the female during intercourse. In one step of the method, the penis may contact a generally planar portion of the insertable member that can be located on the same side of the insertable member as the direction of divergence of the second arced terminus. Contact by the penis with the generally planar portion of the insertable member enhances stimulation of the penis during intercourse. The insertable member can be removed after intercourse is complete.

In one step of the method, the first arced terminus may be inserted into the vagina so that the first arced terminus is oriented toward and contacts an anterior portion of the vaginal wall. In another step of the method, a tapered end of the insertable having a second arced terminus may be oriented so that the second arced terminus protrudes out of the vagina and curves toward the female's anus.

In another step of the method, one or more body parts of the female and male, for example, a Gräfenberg spot, the anterior portion of the vaginal wall, the clitoris, the female anus, and the male's penis, may be stimulated by the inclusion of one or more internal vibrating devices installed within the insertable member. In still another step of the method, the female clitoris may be stimulated by mechanical friction and massaging action produced by a massaging device installed within the insertable member. The massaging device may be a pellet-rotating device. The pellet-rotating device may produce changes in the external texture or circumference of the insertable member. In an exemplary embodiment of this step of the method, the pellet-rotating device can be installed within the tapered end of the insertable member.

The insertable member can be used to enhance and increase the stimulation and pleasure of both sexual partners during intercourse. In other steps of the method, the insertable member may also be manually manipulated by either the female or by another for vaginal penetration and stimulation of the female. To use the insertable member, prior to engaging in sexual intercourse, the insertable member may be lubricated and the bulbous end can be inserted into the vagina. The bulbous end of the insertable member fills and occupies excess space or volume within the vaginal cavity. During intercourse, the male can insert his penis into the female's vagina so that the penis is in frictional contact with the generally planar top side of the insertable member. The generally planar top side may facilitate friction with the penis to increase stimulation of the penile nerve endings, thereby producing a more pleasurable sensation for the male. The large circumference of the bulbous end also stimulates the nerve endings of the vaginal wall during intercourse both by contact with and friction between the vaginal epithelium and the insertable member. The insertable member may also be inserted into the vagina during, rather than prior to, sexual intercourse.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of occupying space within a human female's vagina to provide a fuller sensation to the female and a tighter sensation to a human male's penis within the vagina, the method comprising the steps of: (a) inserting a member into a vagina of a human female to occupy space within the vagina; and (b) maintaining the member inserted within the vagina while the vagina is penetrated by a human penis during sexual intercourse, wherein step (a) of the method further comprises the steps of: (c) inserting a bulbous end of the member comprising a first arced terminus into the vagina so that the first arced terminus is oriented toward and contacts an anterior portion of a wall of the vagina; and (d) orienting a tapered end of the member comprising a second arced terminus so that the second arced terminus protrudes out of the vagina and curves toward the female's anus.

2. The method of claim 1, wherein step (b) of the method further comprises the step of: (e) inserting the penis into the vagina while the member is inserted within the vagina so that the penis contacts both an anterior portion of a wall of the vagina and a generally planar portion of the member.

3. The method of claim 1, wherein the method further comprises at least one step selected from the group consisting of: (f) including a vibrating device in a bulbous end of the member and stimulating a Grafenberg spot inside the vagina using the vibrating device; (g) including a vibrating device in a bulbous end of the member and stimulating an anterior portion of a wall inside of the vagina; (h) including a vibrating device in a bulbous end of the member and stimulating the penis while the penis is inserted into the vagina during sexual intercourse; (i) including a vibrating device in a tapered end of the member and stimulating a clitoris of the vagina; (j) including a vibrating device in a hooked protrusion of the member and stimulating an anus of the human female; and (k) including a pellet-rotating device in a tapered end of the member and stimulating a clitoris of the vagina by mechanical friction as a plurality of pellets are mechanically rotated by a motorized blade within the pellet-rotating device thereby causing changes in the texture of an exterior surface of the member.

4. A sexual aid comprising: an insertable member for removably inserting into a vagina of a human female, the insertable member comprising: a tapered end that is grasped to insert the insertable member into the vagina; a bulbous end that is inserted into the vagina; wherein the bulbous end occupies space thereby reducing the volume of unoccupied space inside the vagina, wherein the insertable member is trough-shaped and comprises a trough defined in a top side.

5. The sexual aid of claim 4, wherein the insertable member is generally elongated, rounded, and flattened in shape, wherein the tapered end is about 1.9 centimeters thick and the bulbous end is about 3.8 centimeters thick.

6. The sexual aid of claim 4, wherein the insertable member comprises silicone.

7. The sexual aid of claim 4, wherein the insertable member is comprised of a memory foam enveloped by an exterior elastomer coating.

8. The sexual aid of claim 7, wherein the memory foam comprises latex memory foam and the exterior elastomer coating comprises latex rubber.

9. The sexual aid of claim 5, wherein the insertable member comprises a tapered end comprising a first arced terminus that curves in a first direction and a bulbous end comprising a second arced terminus that curves in a second direction that is opposite to the first direction.

10. The sexual aid of claim 5, wherein the tapered end comprises a hooked protrusion comprising a spherical terminus.

11. The sexual aid of claim 10, wherein the hooked protrusion is oriented toward the bulbous end.

12. The sexual aid of claim 11, wherein the insertable member is sigmoidal in shape.

13. The sexual aid of claim 4, wherein the insertable member further comprises at least one vibrating device.

14. The sexual aid of claim 5, wherein the tapered end comprises a vibrating device.

15. The sexual aid of claim 10, wherein the bulbous end comprises a vibrating device.

16. The sexual aid of claim 10, wherein the spherical terminus comprises a vibrating device.

17. The sexual aid of claim 13, wherein the at least one vibrating device further comprises a receiver for operation by a remote control.

18. The sexual aid of claim 4, wherein the insertable member comprises a generally planar portion.

19. The sexual aid of claim 5, wherein the tapered end comprises an internal pellet-rotating device.

* * * * *